(12) United States Patent
Marmor (10) Patent No.: US 9,127,008 B2
(45) Date of Patent: Sep. 8, 2015

(54) MORPHINE SULFATE METHANOLIC SOLVATE, PROCESSES FOR MAKING SAME AND RELATED COMPOSITIONS AND METHODS FOR TREATING PAIN

(71) Applicant: Johnson Matthey Public Limited Company, London (GB)

(72) Inventor: Robert S. Marmor, Woodstown, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/212,390

(22) Filed: Mar. 14, 2014

(65) Prior Publication Data

US 2014/0275146 A1 Sep. 18, 2014

Related U.S. Application Data

(60) Provisional application No. 61/791,154, filed on Mar. 15, 2013.

(51) Int. Cl.
*C07D 489/02* (2006.01)
*C07D 489/04* (2006.01)

(52) U.S. Cl.
CPC ............ *C07D 489/02* (2013.01); *C07D 489/04* (2013.01)

(58) Field of Classification Search
None
See application file for complete search history.

(56) References Cited

U.S. PATENT DOCUMENTS

| | | |
|---|---|---|
| 2,062,324 A | 12/1936 | Mallory |
| 5,981,751 A | 11/1999 | Mudryk et al. |
| 6,054,584 A | 4/2000 | Ma et al. |
| 6,387,917 B1 | 5/2002 | Illum et al. |
| 7,671,203 B2 | 3/2010 | Antonini |
| 7,928,234 B2 | 4/2011 | Carroll et al. |
| 8,455,509 B2 | 6/2013 | Dlubala |
| 2008/0241183 A1 | 10/2008 | Palma et al. |
| 2009/0092912 A1 | 4/2009 | Wu et al. |

FOREIGN PATENT DOCUMENTS

| | | |
|---|---|---|
| CN | 1597039 A | 3/2005 |
| GB | 406107 | 2/1934 |
| PL | 129009 | 3/1984 |
| PL | 134180 | 7/1985 |
| WO | 0130321 A1 | 5/2001 |
| WO | WO03074526 | 12/2003 |
| WO | WO2005123743 | 12/2005 |
| WO | WO2006094672 | 9/2006 |
| WO | 2007022609 A1 | 3/2007 |
| WO | WO2009092912 | 7/2009 |

OTHER PUBLICATIONS

Wongweichintana et al.; Structures of morphine methyl iodide monohydrate; Acta Crystallographica; Section C; Crystal Structure Communications; Aug. 15, 1984; vol. 40., No. 8; 1984 IZnternational Union of Crystallography.
Sande et al., Borohydride reducing agent derived from anion exchange resin: selective reduction of α, β-unsaturated carbonyl compounds; Tetrahedron Letters, vol. 25, No. 32, pp. 3501-3504; 1984; Printed in Great Britain; Pergamon Press Ltd.
Proder, Istvan; The Morphine Manufacturing Process of Janos Kabay; Magyar Kemikusok Lapja (1998), 53(4), 169-172; Hungary.
Holzgrabe; Ulrike; 200 Years of Morphine. New Developments from Research; Pharmazeutische Zeitung (2005), 150(40); Germany.

*Primary Examiner* — Timothy R Rozof (57) ABSTRACT

Processes for reducing the amount of impurities, especially α,β-unsaturated ketones (ABUK), in materials containing morphine. Novel compounds, namely low ABUK morphine sulfate methanolic solvate, and a novel crystal form are also described. The method for making morphine sulfate methanolic solvate comprises mixing a morphine free base composition with methanol to form a solution and adding a liquid comprising sulfuric acid to the solution to form a morphine sulfate methanolic solvate precipitate. A method of making a morphine sulfate compound comprises drying the morphine sulfate methanolic solvate in the presence of water vapor, such that methanol molecules are removed and replaced with water vapor molecules. A composition for treating pain comprises the morphine sulfate compound and at least one pharmaceutically acceptable excipient. A method for treating pain comprises administering to a patient in need thereof the composition comprising the morphine sulfate compound and at least one pharmaceutically acceptable excipient.

37 Claims, 5 Drawing Sheets

MORPHINE SULFATE METHANOLIC SOLVATE, PROCESSES FOR MAKING SAME AND RELATED COMPOSITIONS AND METHODS FOR TREATING PAIN

CROSS-REFERENCE TO RELATED APPLICATIONS

This application claims priority of U.S. Provisional Patent Application No. 61/791,154, filed Mar. 15, 2013, the disclosures of which are incorporated herein by reference in their entireties for all purposes.

BACKGROUND OF THE INVENTION

1. Field of Invention

The present invention relates generally to a crystal form of morphine sulfate methanolic solvate, preferably having a low amount of $\alpha,\beta$-unsaturated ketones (ABUK), and methods for making the same. The invention also relates to pharmaceutical compositions containing a morphine sulfate compound and methods for treating pain using such compositions.

2. Description of Related Art

Morphine is the most abundant of at least 50 alkaloids found in opium, poppy and poppy derivatives, *Papaver somniferum*. Poppy straw is opium poppy (*Papaver somniferum*) that is harvested when fully mature and dry, minus the ripe poppy seeds. An agricultural by-product of the poppy seed harvest, the straw was a waste product before the 1930s when a chemical process became available to extract morphine from it. Poppy straw consisting mainly of the capsule became a valuable source of morphine. Today, poppy straw is a major source of many opioids and other alkaloids. It is the source of 90% of the world supply of legal morphine (i.e, for medical and scientific use).

During processing, poppy straw is pulverized and washed many times in water and/or various acids and other chemicals to produce poppy straw concentrate (PSC) or concentrated poppy straw (CPS). Once dried, the concentrate is a beige to brown colored powder and contains salts of various alkaloids. It can range from about 9 to 30 times the morphine concentration of poppy straw. Morphine is generally 8% to 17% of the dry weight of opium, although specially-designed cultivars reach 26% or produce little morphine at all. The latter varieties, including the Przemko and Norman strains of the opium poppy, are used to produce two other alkaloids, thebaine and oripavine, which are used in the manufacture of semi-synthetic and synthetic opioids like oxycodone and etorphine as well as other types of drugs. At least one manufacturer, Tasmanian Alkaloids, produces both high-morphine and high-thebaine/oripavine types of CPS.

Morphine is produced most predominantly early in the life cycle of the plant and, past the optimum point for extraction, various processes in the plant produce codeine, thebaine, and in some cases low quantities of hydromorphone, dihydromorphine, dihydrocodeine, tetrahydrothebaine, and hydrocodone.

Morphine, generally administered in a salt form, is a potent opiate analgesic, for the relief of moderate to severe pain, and has been approved for use for decades. It can be administered as an injectable solution, suppository, capsule, tablet or as an extended release product. Like other opioids, e.g., oxycodone, hydromorphone, and diacetylmorphine (heroin), morphine acts directly on the central nervous system (CNS) to relieve pain. Today, morphine sulfate is sold under various trade names including Astramorph PF, Avinza, Depodur, Infumorph, Kadian, MS Contin and Oramorph SR.

Morphine isolated from the opium poppy or compounds derived therefrom are known to contain ABUK compounds. ABUK, in particular morphinone (morphin-6-on), also forms as a result of morphine degradation. These ABUK compounds are considered to be product impurities. Relatively recently, the United States Food and Drug Administration (USFDA) has identified the ABUK moiety as a structural alert for mutagenicity. As a result, USFDA has required manufacturers of opioid products to decrease the levels of genotoxic ABUK impurities in some of their products. For example, in 2008, the USFDA stated its policy that manufacturers of oxycodone hydrochloride products could be approved before they successfully lowered their levels of 14-hydroxycodeinone (an ABUK) as long as each such manufacturer had an "aggressive" plan to eventually meet USFDA's new, lowered, standard for levels of 14-hydroxycodeinone. More recently, in 2010, USFDA required ABUK levels in oxymorphone hydrochloride products to also be reduced. Thus, there is a trend in the art to reduce ABUK levels in opioid products. There remains a need for methods which permit the formation of morphine with low contamination of ABUK impurities.

All references cited herein, including the morphine sulfate products associated with the above-mentioned trade names, are incorporated herein by reference in their entireties.

BRIEF SUMMARY OF THE INVENTION

The present invention provides methods for producing morphine sulfate methanolic solvate, and low ABUK morphine sulfate methanolic solvate. The invention also provides a crystal form of morphine sulfate methanolic solvate. In addition, the invention provides pharmaceutical compositions containing a morphine sulfate compound made by drying the morphine sulfate methanolic solvate in the presence of water vapor. Such compositions include formulations and dosage forms comprising the morphine sulfate compound and at least one pharmaceutically acceptable excipient. In an embodiment of the present invention, the morphine sulfate methanolic solvate composition has less than 25 ppm of ABUK. Further, the present invention provides methods of treating pain comprising administering a pharmaceutical composition containing the low ABUK morphine sulfate compound. In addition, the present invention provides methods for treating those in need thereof with a low ABUK morphine sulfate compound.

In addition, the present invention provides a method of making a morphine sulfate methanolic solvate having low ABUK comprising mixing a starting composition having morphine and ABUK with alcohol to form a solution whereby at least a portion of the starting composition is dissolved in the alcohol; contacting an anion exchange resin with the solution; separating the resin from the solution; adding water to the solution to produce a morphine free base composition having an ABUK level less than the starting composition; dissolving the morphine free base composition in a methanol solution to form a second solution; and adding sulfuric acid to the second solution to form a morphine sulfate methanolic solvate precipitate.

In an alternative method for making a morphine sulfate methanolic solvate, a morphine free base composition is mixed with methanol to form a solution and then a liquid comprising sulfuric acid (e.g. aqueous sulfuric acid) is added to the solution to form a morphine sulfate methanolic solvate precipitate.

It has been found that the morphine sulfate methanolic solvate is relatively stable compared with other forms of morphine sulfate. In particular, it does not degrade as easily to ABUK (i.e., morphinone). Accordingly, an embodiment of the invention provides a method of making a morphine sulfate compound comprising: mixing a morphine free base composition with methanol to form a solution; adding a liquid comprising sulfuric acid to the solution to form a morphine sulfate methanolic solvate precipitate; and drying the morphine sulfate methanolic solvate in the presence of water vapor, such that methanol molecules are removed and replaced with water molecules to provide the morphine sulfate compound. A preferred embodiment of the invention comprises, between the adding and drying steps, storing the morphine sulfate methanolic solvate for some period of time. In this way, the morphine sulfate is stored in a more stable form.

DETAILED DESCRIPTION OF THE INVENTION

Figure 1:
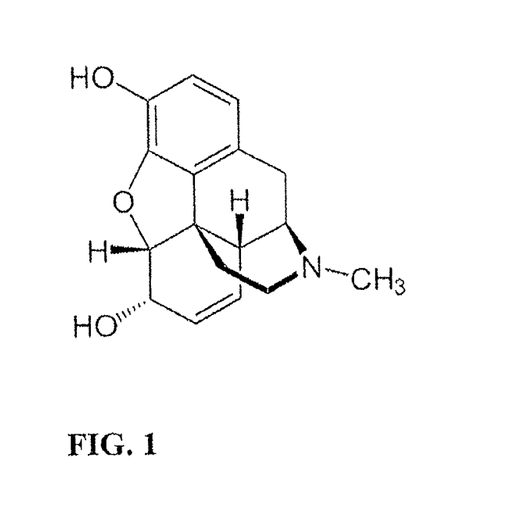
FIG. 1 is a molecular structure representation of morphine.
Figure 2:
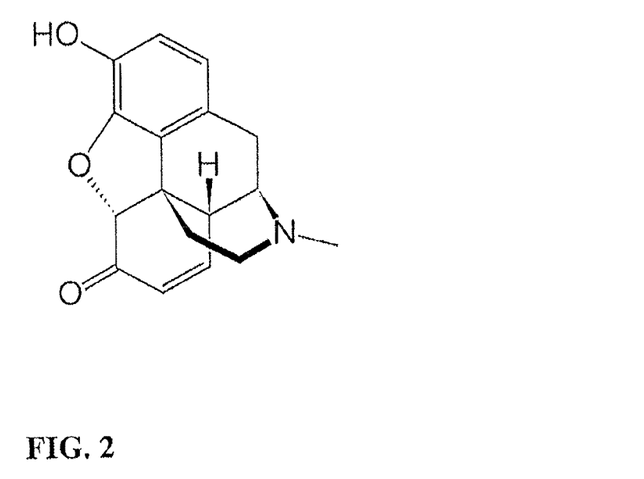
FIG. 2 is a molecular structure representation of morphinone.

Morphine, shown structurally in FIG. 1, is regarded as the gold standard or benchmark of analgesics used to relieve severe or agonizing pain and suffering. However, raw or starting materials that contain morphine are known to also contain various impurities. For example, Turkish CPS, which typically contains about 90-93% morphine, also contains about 4-6% codeine in addition to various amounts of 10-hydoxymorphine, morphine N-oxide, normorphine, morphinone, oripavine, apomorphine, and psuedomorphine. Also, Australian CPS, which tends to be naturally low in codeine (<0.10%), also contains several impurities. Morphinone, shown structurally in FIG. 2, is a known ABUK compound. Also, other impurities can be ABUK precursors such that they form ABUK compounds (e.g., morphinone) during processing. The present invention provides, among other aspects, an improved method of purifying materials that contain morphine.

The inventor has found a way to remove at least a portion of the impurities contained in materials containing morphine by converting them to ABUK and then using an anion exchange resin to remove a significant amount of the ABUK in order to provide a low ABUK morphine compound. The morphine compound can also be converted to a sulfate methanolic solvate and, in so doing, remain relatively low in ABUK content.

In an embodiment of the invention, a method of reducing the amount of impurities, including ABUK, in a composition comprising morphine is provided. The method includes processing a raw material that contains morphine and various impurities, including ABUK. Preferably, this method includes combining CPS, an alcohol solution and water to ultimately form a precipitate comprising morphine and ABUK. Most preferably, the water is deionized water.

Optionally, the method also includes not starting with a raw material such as CPS but instead starting with a more processed composition comprising morphine. The composition is mixed with water and an acid until at least a portion of the composition dissolves. The mixture is heated for a time sufficient for the composition to react with the water and acid, and a base is added until a precipitate forms. The precipitate is filtered to provide a starting morphine composition having ABUK.

More specifically, in an embodiment for reducing the amount of ABUK in a composition comprising morphine, the composition having an initial level of ABUK is mixed with an alcohol solution, most preferably a methanol solution, such that a portion of the composition is dissolved in the solution. Preferably, the solution is heated during the mixing, more preferably to about 50° C.-60° C. and, most preferably, it is heated to a temperature such that all of the starting composition dissolves in the alcohol solution. The solution is then contacted with an anion exchange resin, preferably an anion exchange resin loaded with borohydride. Of course, it is important that the borohydride remain fresh; it has been found that it can deteriorate, in which case ABUK is not as readily reduced. After the solution has been placed in contact with the resin for a sufficient amount of time, it is separated from the resin. Preferably, the solution is in contact with the resin for at least 10 hours, more preferably 20 to 72 hours. Water is added to the solution to ultimately produce a morphine free base composition as a precipitate having a reduced level of ABUK.

The resultant morphine free base composition can be separated from the solution by a variety of conventional means including filtering. Optionally, activated carbon can be added to the process, preferably prior to or during mixing the morphine composition with the alcohol, as it is has been shown to be able to remove undesirable color from the composition. The activated carbon is eventually removed from the process.

In another embodiment of the invention, a method of making a morphine sulfate methanolic solvate is provided and includes the steps described above for providing a morphine free base composition having a reduced level of ABUK. Specifically, a composition having an initial level of ABUK is mixed with an alcohol solution, preferably heated, and contacted with an anion exchange resin for a sufficient amount of time before adding water to the resin-treated solution to ultimately produce a morphine free base composition having a reduced level of ABUK. The embodiment further includes mixing the resultant morphine free base composition having a reduced level of ABUK with methanol to form a solution and adding sulfuric acid to the solution to form a morphine sulfate methanolic solvate precipitate. Preferably, the solution is heated while the morphine composition is mixed in methanol. More preferably, the solution is heated to at least 50° C. and, most preferably, it is heated to a temperature such that all of the composition dissolves in the alcohol. The possibility exists that crystals will not form after the acid is added to the methanol/morphine solution. In order to initiate crystal formation, a portion of the solution may need to be withdrawn, placed in, e.g., a beaker and "scratched" by, for example, dragging a spatula across a portion of the beaker submerged in the solution until crystals form. The removed solution, with crystals, can then be combined with the remainder of the solution.

In another embodiment of the invention, a method of making a morphine sulfate methanolic solvate is provided and includes starting with a morphine free base composition, preferably having a reduced level of ABUK, and mixing with methanol to form a solution and adding sulfuric acid to the solution to form a morphine sulfate methanolic solvate precipitate. The morphine free base composition could be prepared by the method described above or otherwise as is known in the art. Preferably, the solution is heated while the morphine composition is mixed in methanol. More preferably, the solution is heated to at least 50° C. and, most preferably, it is heated to a temperature such that all of the composition dissolves in the alcohol. The possibility exists that crystals will not form after the acid is added to the methanol/morphine solution. In order to initiate crystal formation, a portion of the solution may need to be withdrawn, placed in, e.g., a beaker and "scratched" by, for example, dragging a spatula across a portion of the beaker submerged in the solution until crystals form. The removed solution, with crystals, can then be combined with the remainder of the solution.

The processes of the invention are highly flexible, permitting many reaction steps to be carried out without isolation of intermediate products, while still retaining high (greater than 50%) overall yields as well as remarkably high purity. Under favorable conditions, the presence of ABUK is undetectable by conventional means such as HPLC, but the skilled person can readily achieve less than 25 ppm ABUK contamination in both the morphine free base and the morphine sulfate methanolic solvate.

In another aspect of the invention, low ABUK morphine products are provided. In one embodiment, the invention provides a morphine free base composition having less than 10 ppm of ABUK. In a different embodiment, a morphine sulfate methanolic solvate composition is provided having less than 25 ppm of ABUK. Preferably, the morphine sulfate methanolic solvate having less than 25 ppm of ABUK contains from about 7% to about 10% by weight methanol as determined by gas chromatography and from about 1% to 5% water by weight as determined by Karl Fischer. More preferably, the solvate contains about 8% to 9% by weight methanol and about 2% to 3% by weight water.

Figure 3:
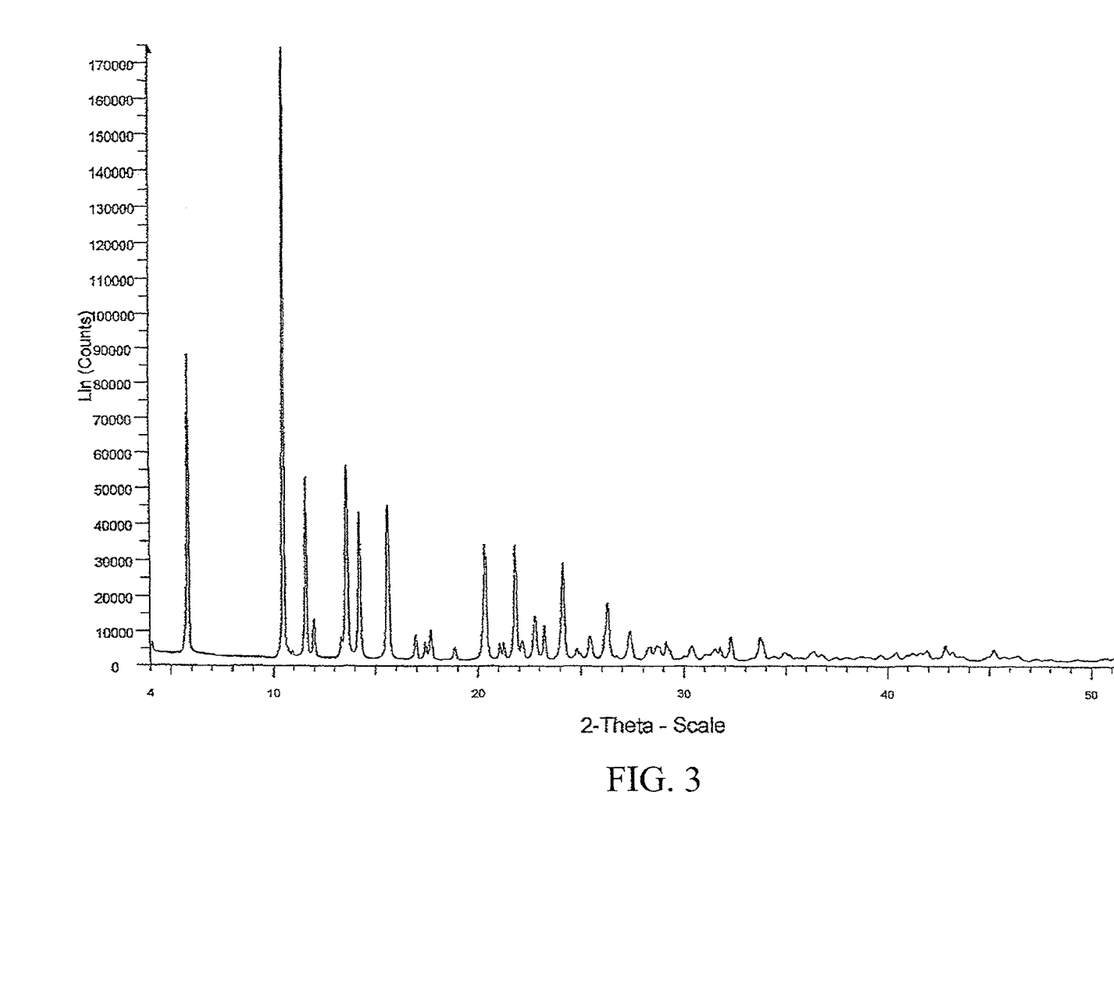
FIG. 3 is an x-ray powder diffraction (XRPD) pattern collected from a morphine sulfate pentahydrate sample.

Also, preferably, the morphine sulfate methanolic solvate is in a crystalline (not amorphous) form. The results comparing this low ABUK morphine sulfate methanol solvate product to morphine sulfate pentahydrate confirmed that the methanol solvate product has a defined crystalline structure which is different from the morphine sulfate pentahydrate crystal structure. This difference is clearly shown by comparing the XRPD diffractogram for morphine sulfate pentahydrate shown in FIG. 3 to the XRPD diffractogram for the morphine sulfate methanol solvate shown in FIG. 4. Thus, the inventor has discovered a new crystal form. The XRPD peaks (in degrees 2θ) for the morphine sulfate methanol solvate product and their respective intensities, percent intensities, and d-values are shown below in Table A. Accordingly, not only can the crystalline morphine sulfate methanolic solvate of the present invention be identified by its XRPD pattern, but it can also be identified by the data provided in Table A. As shown in Table A, characteristic peaks of the crystalline morphine sulfate methanolic solvate of the present invention include those having degrees 2θ of about 9.31, 9.56, 10.75, 13.47, 14.30, 16.36, and 23.49, or, about 9.3, 9.6, 10.7, 13.5, 14.3, 16.4, and 23.5. In an embodiment of the invention, morphine sulfate methanolic solvate of the present invention has at least one peak, and preferably at least three peaks, at degrees 2θ of about 9.31, 9.56, 10.75, 13.47, 14.30, 16.36, and 23.49, or about 9.3, 9.6, 10.7, 13.5, 14.3, 16.4, and 23.5. Most preferably, morphine sulfate methanolic solvate of the present invention has at least one peak at degrees 2θ of about 9.31, 9.56, 10.75, 13.47, 14.30, 16.36, and 23.49, or about 9.3, 9.6, 10.7, 13.5, 14.3, 16.4, and 23.5.

TABLE A

Morphine Methanol Solvate 2405-23

Figure 4:
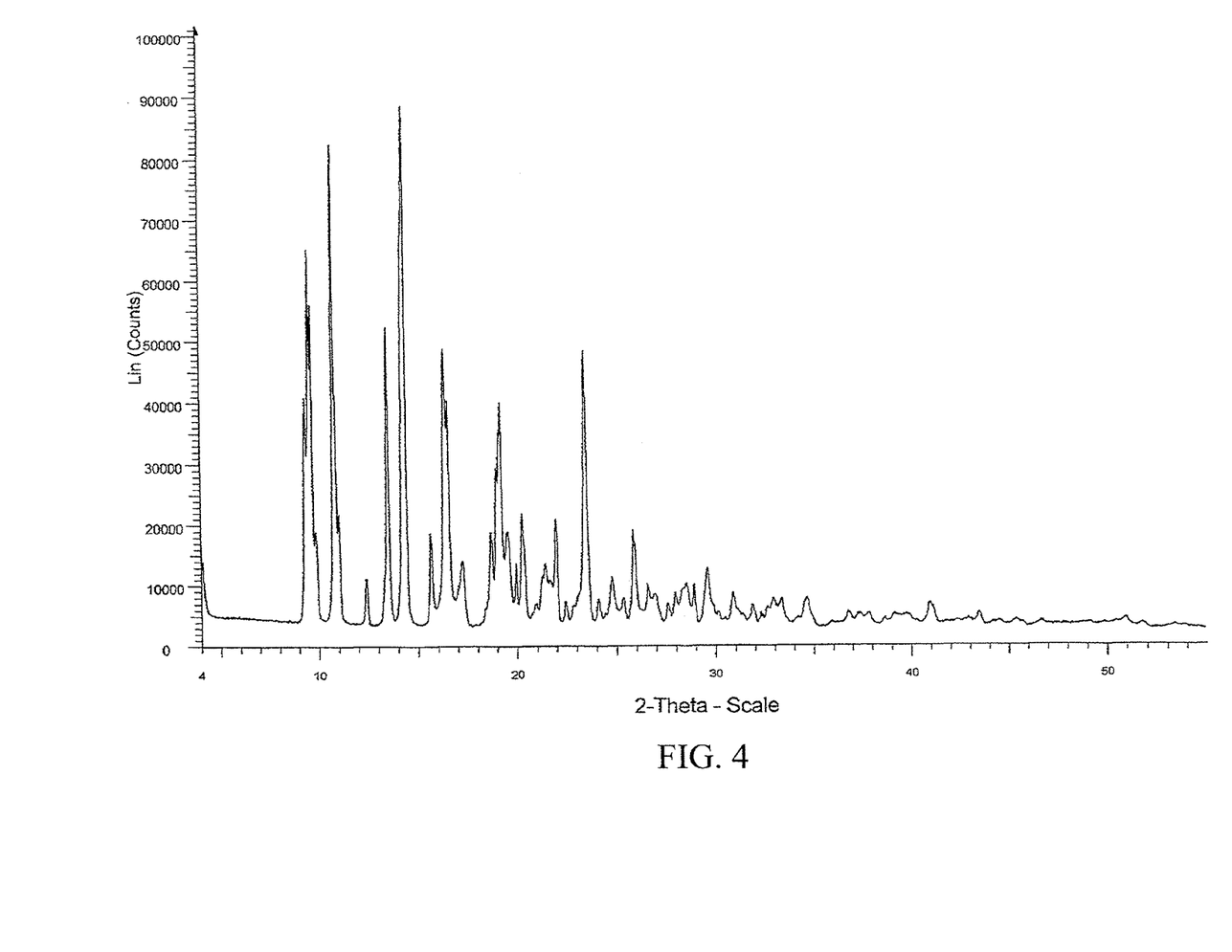
FIG. 4 is an XRPD pattern collected from a morphine sulfate methanolic solvate product sample made according to Example 10.

| Angle 2-Theta | Intensity | Intensity % | d-value |
|---|---|---|---|
| 10.75 | 37278 | 100 | 8.21 |
| 14.30 | 35957 | 96.5 | 6.18 |
| 13.47 | 24699 | 66.3 | 6.56 |
| 9.56 | 24051 | 64.5 | 9.24 |
| 23.49 | 23704 | 63.6 | 3.78 |
| 16.36 | 22542 | 60.5 | 5.41 |
| 9.31 | 22534 | 60.4 | 9.48 |
| 19.19 | 16201 | 43.5 | 4.61 |
| 19.01 | 10892 | 29.2 | 4.66 |
| 20.29 | 10131 | 27.2 | 4.37 |
| 19.51 | 9667 | 25.9 | 4.54 |
| 18.67 | 8823 | 23.7 | 4.74 |
| 9.88 | 7705 | 20.7 | 8.94 |
| 25.87 | 7212 | 19.3 | 3.44 |
| 17.19 | 6926 | 18.6 | 5.15 |
| 21.96 | 6909 | 18.5 | 4.04 |
| 21.4 | 6815 | 18.3 | 4.14 |
| 29.61 | 6066 | 16.3 | 3.01 |
| 15.62 | 6050 | 16.2 | 5.66 |
| 21.64 | 5801 | 15.6 | 4.10 |
| 12.36 | 5627 | 15.1 | 7.15 |
| 24.77 | 5526 | 14.8 | 3.59 |
| 28.54 | 4957 | 13.3 | 3.12 |
| 19.96 | 4866 | 13.1 | 4.44 |
| 28.35 | 4612 | 12.4 | 3.14 |
| 26.61 | 4323 | 11.6 | 3.34 |
| 26.91 | 4184 | 11.2 | 3.30 |
| 23.04 | 4086 | 11.0 | 3.85 |
| 28.01 | 3799 | 10.2 | 3.18 |
| 28.91 | 3820 | 10.2 | 3.08 |
| 32.95 | 3820 | 10.2 | 2.71 |
| 25.32 | 3671 | 9.8 | 3.51 |
| 20.93 | 3531 | 9.5 | 4.24 |
| 30.91 | 3546 | 9.5 | 2.89 |
| 34.66 | 3435 | 9.2 | 2.58 |
| 22.87 | 3224 | 8.6 | 3.88 |
| 33.34 | 3148 | 8.4 | 2.68 |
| 40.97 | 3094 | 8.3 | 2.20 |
| 24.08 | 3008 | 8.1 | 3.69 |
| 22.45 | 2965 | 8.0 | 3.95 |
| 32.65 | 2881 | 7.7 | 2.74 |
| 27.59 | 2690 | 7.2 | 3.23 |
| 31.87 | 2650 | 7.1 | 2.80 |
| 37.79 | 2563 | 6.9 | 2.37 |
| 43.48 | 2530 | 6.8 | 2.07 |
| 31.33 | 2538 | 6.8 | 2.85 |
| 39.18 | 2504 | 6.7 | 2.29 |
| 37.37 | 2406 | 6.5 | 2.40 |
| 36.82 | 2434 | 6.5 | 2.43 |
| 30.13 | 2381 | 6.4 | 2.96 |
| 32.32 | 2265 | 6.1 | 2.76 |
| 39.82 | 2242 | 6.0 | 2.26 |
| 34.20 | 2180 | 5.8 | 2.61 |
| 50.91 | 1975 | 5.3 | 1.79 |
| 38.64 | 1984 | 5.3 | 2.32 |
| 42.83 | 1889 | 5.1 | 2.10 |
| 45.41 | 1793 | 4.8 | 1.99 |
| 46.71 | 1776 | 4.8 | 1.94 |
| 36.15 | 1751 | 4.7 | 2.48 |
| 44.50 | 1744 | 4.7 | 2.03 |
| 44.35 | 1767 | 4.7 | 2.04 |
| 35.97 | 1732 | 4.6 | 2.49 |
| 45.67 | 1720 | 4.6 | 1.98 |
| 49.14 | 1630 | 4.4 | 1.85 |
| 49.82 | 1623 | 4.4 | 1.82 |
| 47.89 | 1550 | 4.2 | 1.89 |
| 51.83 | 1519 | 4.1 | 1.76 |
| 53.85 | 1419 | 3.8 | 1.70 |
| 53.39 | 1423 | 3.8 | 1.71 |
| 53.11 | 1384 | 3.7 | 1.72 |

Figure 5:
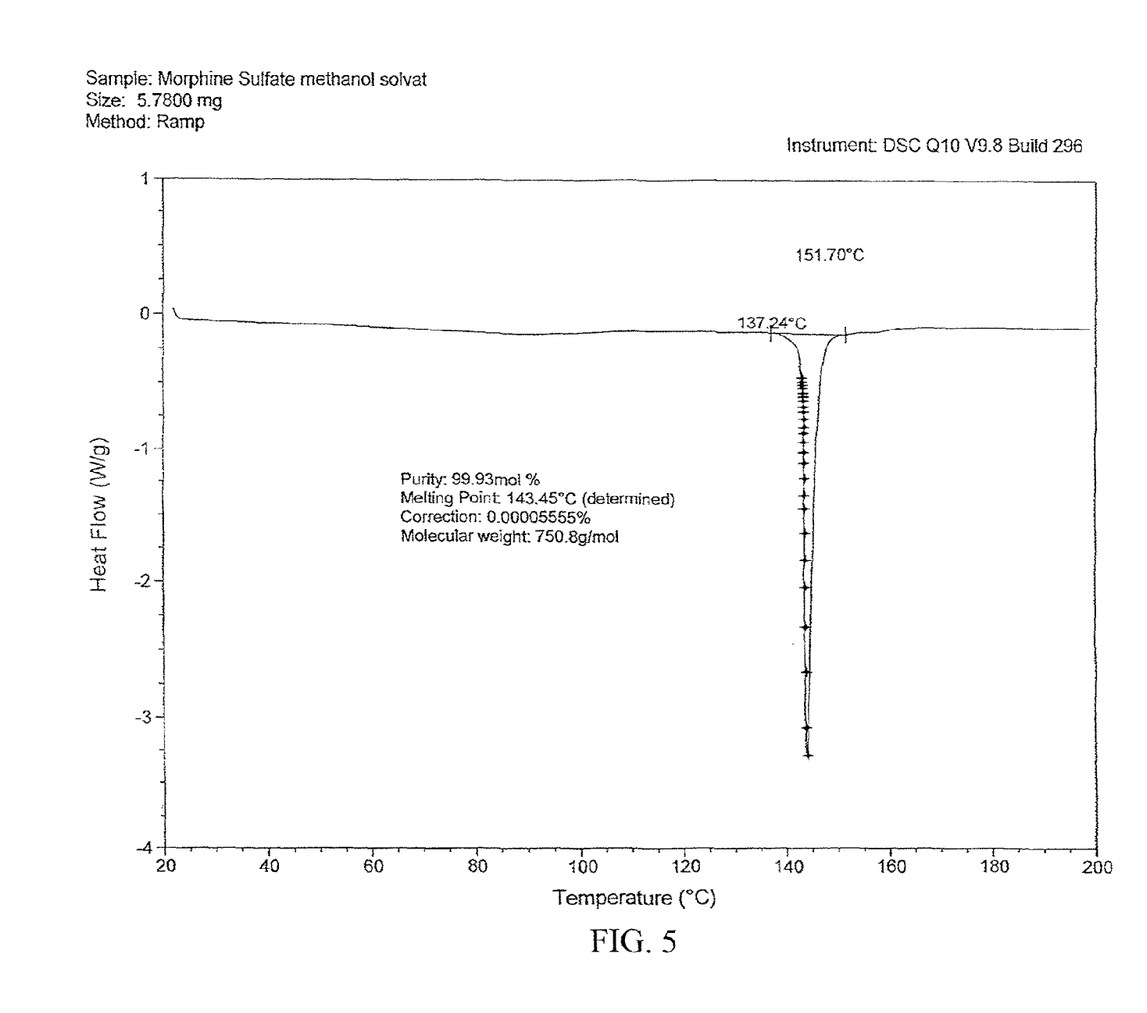
FIG. 5 is a differential scanning calorimetry (DSC) graph collected from a morphine sulfate methanolic solvate product sample also made according to Example 10.

Additionally, as shown in FIG. 5, the crystalline morphine sulfate methanolic solvate of the present invention can also be identified by its differential scanning calorimetry (DSC) curve. In particular, it has been demonstrated that the solvate has a melting point onset temperature of about 137.2° C. and a melting point temperature of about 143.4° C., both temperatures determined by DSC.

As formed, the morphine sulfate methanolic solvate has from about 7% to about 10% by weight methanol. As methanol at high levels is known to be toxic, it is desirable to remove the methanol either entirely or to an amount below about 0.15% by weight. Accordingly, the present invention provides a method for providing a substantially methanol-free morphine sulfate compound comprising making morphine sulfate methanolic solvate as described herein, then reducing the methanol content. One way of doing so is by drying the morphine sulfate methanolic solvate in the presence of water vapor, such that methanol molecules are removed and displaced or replaced with water vapor molecules. Any suitable drying method can be used, such as that described in U.S. Pat. No. 5,981,751, incorporated herein by reference.

The product formed is characterized herein as a morphine sulfate compound, and could include no or substantially no methanol or some detectably amount of methanol but no more than 0.15% by weight, preferably less than 0.10% by weight, and most preferably less than 0.05% by weight. In an embodiment of the invention, the morphine sulfate compound formed is a crystalline morphine product containing water and methanol molecules and having less than 0.15% by weight methanol, preferably less than 0.10% by weight methanol, and most preferably preferably less than 0.05% by weight methanol. The morphine sulfate product formed may have a regular, repeating crystalline structure having water and methanol molecules in the crystal structure or it may have various phases of different crystal structures having varying amounts of water and methanol molecules (including none in some phases) or it may include some amorphous phases, optionally with some water and methanol molecules associated with such amorphous phases. In any event, at least some methanol molecules will likely remain, although preferably, the drying continues until all or substantially all of the methanol is driven off. Some water molecules will be in the final morphine sulfate product, regardless of the form.

As shown by the examples below, the morphine sulfate methanolic solvate is relatively stable compared with other forms of morphine sulfate. In particular, it does not degrade as easily to ABUK (i.e., morphinone). Accordingly, an embodiment of the invention provides a method of making a morphine sulfate compound comprising: mixing a morphine free base composition with methanol to form a solution; adding a liquid comprising sulfuric acid to the solution to form a morphine sulfate methanolic solvate precipitate; storing the morphine sulfate methanolic solvate for some period of time; and drying the morphine sulfate methanolic solvate in the presence of water vapor, such that methanol molecules are removed and replaced with water molecules to provide the morphine sulfate compound. In this way, the morphine sulfate is stored, for example for up to 18 months, more preferably between 1 day and 15 months, more preferably between 2 weeks and 1 year, more preferably between 1 month and 9 months, and most preferably between 2 and 6 months in this more stable form. After this storage period, which preferably is in an inert atmosphere, the morphine sulfate methanolic solvate is dried as described above to provide a morphine sulfate compound and it is then formulated into a pharmaceutical composition by combining the morphine sulfate compound and at least one pharmaceutically acceptable excipient, in a known manner. Preferably, the formulation step occurs promptly after drying step to minimize degradation of the morphine sulfate compound. Preferably, the formulating step is carried out within one week, more preferably within two days, more preferably within one day, more preferably within 12 hours, and most preferably within one hour, after the completion of the drying step. Thereafter, the pharmaceutical composition is stored, preferably in an inert atmosphere, such as in nitrogen or argon.

The morphine sulfate compound of the present invention can be incorporated into dosage forms or pharmaceutical compositions, e.g., by admixtures of the morphine sulfate compound having low ABUK levels with conventional excipients, i.e., pharmaceutically acceptable organic or inorganic carrier substances. Specific examples of pharmaceutically acceptable carriers and excipients that may be used to formulate oral dosage forms are described in various editions of the Handbook of Pharmaceutical Excipients, American Pharmaceutical Association.

For oral formulations, the dosage forms can provide a sustained release of the active component. Suitable pharmaceutically acceptable carriers include those already known in the art and those yet to be discovered. Also, the compositions intended for oral use may be prepared according to any method known in the art as well as yet to be discovered improvements thereto, and such compositions may contain one or more agents selected from the group consisting of inert, non-toxic pharmaceutically acceptable excipients that are suitable for the manufacture of tablets, capsules, solutions, or suspensions.

The sustained release dosage forms may optionally comprise particles containing the low ABUK products of the present invention. Preferably, the particles are film coated with a material that permits release of the active at a sustained rate in an aqueous medium. The film coat is chosen so as to achieve, in combination with the other stated properties, desired release properties. The sustained release coating formulations of the present invention should preferably be capable of producing a strong, continuous film that is smooth and elegant, capable of supporting pigments and other coating additives, non-toxic, inert, and tack-free.

Coated bead technology for achieving sustained release products is also encompassed in the present invention as is the use release-modifying agents and erosion-promoting agents. Also, the sustained release coatings of the present invention may include an exit means comprising at least one passageway, orifice, or the like. Further, a sustained release formulation can be achieved via a matrix optionally having a sustained release coating. In addition to the above ingredients, a sustained release product may also contain suitable quantities of other materials, e.g. diluents, lubricants, binders, granulating aids, colorants, flavorants and glidants that are conventional in the pharmaceutical art.

The sustained release formulations of the present invention preferably slowly release the active agent(s), e.g. when ingested and exposed to gastric fluids, and then to intestinal fluids. The sustained release profile of the formulations of the invention can be altered, for example, by varying the amount of retardant, i.e., hydrophobic material, by varying the amount of plasticiser relative to hydrophobic material, by the inclusion of additional ingredients or excipients, by altering the method of manufacture, etc. Sustained release dosage forms according to the present invention may also be prepared as osmotic dosage formulations known in the art as well as improvements thereto.

The formulations of the present invention may be formulated as a pharmaceutical suppository for rectal administration comprising a suitable suppository base, and the low ABUK products of the present invention. This includes the preparation of sustained release suppository formulations is described in, e.g., U.S. Pat. No. 5,215,758.

In certain embodiments, the present invention provides for a method of treating pain by administering to a mammal in need thereof the dosage forms described herein which contain the low ABUK morphine sulfate compound of the present invention. Those dosage forms used to treat humans will typically be in either an injectable or capsule form. Preferably, the injectable form contains from about 0.1 mg/mL to about 25 mg/mL morphine, most preferably from about 0.5 mg/mL to about 15 mg/mL morphine. Also, preferably, the capsule form contains from about 1 mg to about 250 mg morphine, most preferably from about 10 mg to about 200 mg morphine.

The invention will be illustrated in more detail with reference to the following embodiments and examples, but it should be understood that the present invention is not deemed to be limited thereto. For example, subject to regulatory approval, the morphine ingredients or products of the present invention having low ABUK levels may be used as a substitute for the morphine used as the active ingredient in existing commercial products including, e.g., Astramorph PF, Avinza, Depodur, Infumorph, Kadian, MS Contin and Oramorph SR. Such formulations are listed in the FDA Orange Book and are incorporated herein by reference.

EXAMPLES

Example 1

Recrystallization of Morphine Base

A 2-liter flask equipped with magnetic stirring was charged with 178.54 g Turkish CPS and 1626 ml methanol. A mixture of four different CPS lots ranging from about 70-95% by weight morphine was used for the experiment. Based on analyses of the components, the charge contained 142.67 grams AMA (500 mmoles) and 24.1 grams water. The total amount of methanol used was 12 ml for every gram of AMA, 95% of this is charged and the remaining 5% portion was saved for transfer and filter wash.

The solution was warmed to 55-60° C. during which the CPS was observed to completely dissolve. Norit CA3 activated carbon (9.99 grams) was added. The activated carbon charge was 0.07 grams carbon per gram AMA. The mixture was stirred vigorously for 10 minutes, then filtered quickly through a methanol-moistened bed of Celite directly into a 3-liter 3-neck round bottom flask (RBF), followed by an 86 ml warm methanol rinse. It is noted that the morphine may come out of solution if the filtration operation is not done quickly. Vacuum filtration was used, and an effort was made to close the vacuum line as soon as it was not needed to minimize methanol loss.

The flask was equipped with mechanical stirring, a dropping funnel, a temperature probe and a heating mantle, and was placed under nitrogen. The mixture was stabilized at 55-60° C. and the dropping funnel was charged with 233 ml water. The water charge was 1.8 ml water per gram AMA, corrected for the water already present in the mixture; in other words, sufficient water was added such that the total charge of water, was 1.8 ml water per gram AMA. The water was added over 30 minutes, maintaining the temperature at 55-60° C. during which a precipitate of morphine was observed to form. The mixture was stirred at 55-60° C. for one hour, and then slowly cooled over a two hour period to 0 to 5° C. The mixture was filtered, using some of the filtrate to assist with the transfer. The morphine crystals were washed with 185 ml of an ice-cold solution of 20% water in methanol. 1.3 ml of an ice-cold solution of 20% water in methanol was used per gram AMA.

The wet cake weight of the product was 151.2 grams. The cake was placed in a vacuum oven at about 60° C. overnight. The dried weight was 130.38 grams resulting in a 87.5% yield based on moles morphine. Liquid chromatography determined the area percent of morphine was 98.94% and codeine was 0.48%. Karl Fischer analysis determined the product contained 3.27% water and a ColorEye test result of 88.3 (off-white) was made. The product also contained 65 ppm ABUK as morphinone.

Example 2

Second Recrystallization

A 2-liter flask equipped with magnetic stirring was charged with 127.3 g of the once-recrystallized morphine of Example 1 and 1677 ml methanol. It is noted that the charge was estimated to actually contain 124.8 g AMA and 0.6 grams water. Also, the total methanol used was 14 ml for every gram of AMA, 96% of this was to dissolve the morphine, 2% was to wash the activated carbon, and 2% was to wash borohydride resin. (It is noted that, when 13 ml methanol per gram AMA was used, morphine precipitated out during the borohydride treatment process and fouled the resin.)

The solution was warmed to 55-60° C. The morphine completely dissolved. Norit CA3 activated carbon (8.74 grams) was added (0.07 grams carbon per gram AMA). The mixture was stirred vigorously for 10 minutes, then filtered quickly through a methanol-moistened bed of Celite directly into a 3-liter flask followed by a 35 ml warm methanol rinse. It is again noted that morphine may come out of solution if the filtration operation is not done quickly. Vacuum filtration was used, and an effort was made to close the vacuum line as soon as not needed to minimize methanol loss.

Borohydride resin (5.74 grams) was added to reduce the morphinone level and the mixture was stirred at 47-53° C. for 18 hours. The resin was Aldrich #328642 Amberlite IRA-400 ion exchange resin loaded with 3.8 mmols borohydride per gram of resin. The mixture was filtered through a coarse fritted glass filter directly into a 3-liter 3N RBF followed by a 35 ml warm methanol rinse. The flask was equipped with mechanical stirring, a dropping funnel, a temperature probe and a heating mantle, and was placed under nitrogen. The mixture was stabilized at 55-60° C. and the dropping funnel was charged with 262 ml water. The water charge was 2.1 ml water per gram AMA, corrected for the water present in the once-recrystallized morphine. The water was added over 30 minutes, maintaining the temperature at 55-60° C., during which a precipitate of morphine forms. The mixture was stirred at 55-60° C. for one hour, then slowly cooled over a two hour period to 0 to 5° C. The mixture was filtered, using some of the filtrate to assist with the transfer. The morphine crystals were washed with 162 ml of an ice-cold solution of 20% water in methanol (1.3 ml of an ice-cold solution of 20% water in methanol is used per gram AMA). The wet cake weight was 128.98 grams. The cake was placed in a 60° C. vacuum oven for 45 hours. The dried weight was 110.03 grams, an 87.6% yield based on moles morphine. Liquid chromatography determined the area percent of morphine was 99.69% and codeine was 0.06%. Karl Fischer analysis determined the product contained 0.29% water and an ColorEye test result of 96.0 (white) was made. The product contained 22 ppm ABUK as morphinone.

Example 3

Morphine Free Base: Acid Pretreatment 50.0 grams of morphine base material (MW 285.34, 175.2 mmol on 100% basis, 85 ppm ABUK) and 250 ml of deionized water were charged in a 1 liter flask fitted with a condenser apparatus having a temperature probe and a pH probe. The morphine and water were mechanically stirred under an inert gas of nitrogen to produce a mixture with a pH of 8.54 at room temperature and pressure. Next, 48.2 ml of about 51% sulfuric acid ($H_2SO_4$) (7.28 M, 351 mmol, 702 mmol $H^+$) was added to the mixture during which the morphine was observed to dissolve at about a pH of 1.38. The temperature of the mixture was increased to 60° C. and the mixture was stirred for about 2 hours after which it was cooled to 20° C. resulting in a slurry. The slurry was neutralized to a target pH of 8.5 with 343 ml 2 M sodium hydroxide (NaOH) solution during which the pH was observed to increase to 10.57 at the end of the neutralization process. As a result, 150 ml of 1.2 M of $NaHCO_3$ was added to lower the pH to 8.71 and the slurry was stirred for about 30 minutes. Next, the morphine was filtered from the slurry and washed with water resulting in 135.0 grams of a wet morphine base cake material. The material was transferred to a crystallizing dish and placed in a vacuum oven at 60° C. After several hours the material had a mass of 47.32 grams and an ABUK (e.g., morphinone) level of 109 ppm.

Example 4

Low ABUK Morphine Free Base

| Ingredient | Basis | Amount Used |
| --- | --- | --- |
| AMA | 1 gram | 45.8 grams |
| methanol | 15 ml | 687 ml |
| water (deionized) | 2.25 ml | 103 ml |
| activated carbon | 0.07 grams | 3.2 grams |
| resin | 0.046 grams | 2.1 grams |

The morphine base (45.8 grams, 109 ppm ABUK) of Example 3 was dissolved in 595 ml of methanol (13 to 1 ratio, ml of solvent to grams of base) at 50° C. An additional 46 ml of methanol was added to the mixture resulting in about a 14 to 1 ratio and the temperature was increased to 60° C. in order to dissolve the morphine. The activated carbon was added and the mixture was stirred for about 5 minutes. The mixture was then washed (using methanol) through a methanol-moist Celite bed filter directly into a 1 liter round-bottom flask (RBF). This resulted in a methanol to base ratio of about 15 to 1.

The resin was added to the mixture under an inert gas of nitrogen such that the mixture was contained in a flask having a mechanical stirrer, temperature probe and condenser. The resin was Amberlite IRA-400 loaded with 2.5-5.0 mmol of borohydride per gram of resin (Aldrich #328642). The mixture was stirred over night at 50° C. Next, the mixture was quickly filtered into a 1 liter RBF and the temperature was increased to 60° C. Water was then added to the mixture over a period of about 15 minutes while maintaining the temperature at 60° C. A precipitate was observed to form toward the end of the water addition. The slurry was stirred for about 1 hour at 60° C., then cooled to 0-5° C. over about 1 hour. Next, the slurry was filtered and the solids were washed with 100 ml of cold 20% water in methanol. This resulted in a wet cake of 54.3 grams of morphine base which was placed in a vacuum oven at 60° C. for about an hour. The mass of the morphine base was then determined to be 44.3 grams. The morphine was then transferred to a crystallizing dish and placed back in the oven after which was weighed again and determined to be 42.87 grams. The morphine base product contained 19 ppm ABUK.

Example 5

Morphine Sulfate Pentahydrate

| Ingredient | Basis | Amount Used |
| --- | --- | --- |
| AMA | 1 gram | 20.0 grams |
| water (deionized) | 2.52 grams | 50.4 grams |
| SDA 3A | wash | 40 ml |
| sulfuric acid (51%) | 5.0 ml | 4.5 ml |

Morphine free base material (AMA) from Example 4 (19 ppm ABUK) and water were mixed, heated to 55° C. and the pH was determined to be 7.75. The following titration was performed using sulfuric acid (51%) as the temperature was increased to about 65° C.

Titration

| ml acid added | pH | temperature (° C.) |
| --- | --- | --- |
| 0 | 7.75 | 55 |
| 1.0 | 6.08 | 59 |
| 2.0 | 5.50 | 63 |
| 3.0 | 5.30 | 65 |
| 4.0 | 5.09 | 65.2 |
| 4.5 | 4.63 | 65.3 |

The mixture was then cooled back down to a temperature of 55° C. over about a 20 minute period during which an unacceptably thick precipitate formed. As a result, the temperature was increased again to 65° C. forming a milky mixture or solution. The mixture was then cooled to 57° C. over about a 20 minute period, after which the temperature of the mixture was reduced to about 0-5° C. over about a 2 hour period. The precipitate that formed was then filtered and washed with about 70 ml of denatured ethanol (SDA 3A). The filtered wet cake (29.29 grams) was placed in a vacuum oven at 60° C. overnight and weighed (21.04 grams). The dried cake was then transferred to a crystallizing dish, placed back in the oven for about an hour and then weighed (20.9 grams) and bottled. Analysis of the material indicated the level of ABUK was 64 ppm.

Example 6

Morphine Sulfate Prepared in Ethanol 10.0 grams of low ABUK (19 ppm) morphine base from Example 4, 150 ml of 200 proof ethanol, and 6.3 ml of water were charged in a 500 ml flask fitted with a condenser apparatus, a temperature probe and a pH probe. The mixture was mechanically stirred under an inert gas of nitrogen and brought to a reflux. An additional 100 ml (two 50 ml increments) of ethanol was added to the mixture in an effort to dissolve the morphine base after which the mixture was returned to reflux. After being cooled to 50° C., the temperature of the mixture was increased to 65-70° C. and the base remained in solution. Next, 1 gram of the morphine sulfate from Example 2 was added to the mixture in an effort to direct the formation of crystalline morphine sulfate pentahydrate. Much, but not all, of the morphine sulfate dissolved in the mixture. Next, 51% sulfuric acid was added to the mixture to adjust the pH to a target of 4.5-5.0. The titration, which was conducted under nitrogen at a temperature of 65-70° C., slightly exceeded the target and resulted in a precipitate and a pH of 3.14. The slurry was then stirred for 30 minutes after which it was cooled to 0-5° C. over an hour period. The precipitate was filtered, washed with 100 ml of ethanol (two 50 ml increments), transferred to a crystallization dish and placed in a vacuum oven at 60° C. to dry.

After two hours in the oven the morphine sulfate contained 17 ppm ABUK, 5.25% water (by Karl Fischer) and 0.95% ethanol (by gas chromatography). Next, the morphine sulfate was placed in a moisturizing chamber which contained a constant flow of moist, room temperature air. After several days in the chamber the morphine sulfate was analyzed and determined to contain 123 ppm ABUK, 9.8% water and 0.11% ethanol.

Example 7

Morphine Free Base: No Acid Pretreatment 50.0 grams of morphine base material (MW 285.34, 175.2 mmol on 100% basis, 85 ppm ABUK) and 700 ml of methanol were charged in a 1 liter flask fitted with a condenser apparatus, and a temperature probe. The mixture was mechanically stirred under an inert gas of nitrogen and heated to 60° C. to dissolve the base. Activated carbon (3.5 grams) was added to the flask after which stirring continued for about 5 minutes. Next, the mixture containing carbon was filtered through a Celite filter while rinsing with methanol (50 ml) to aid the transfer of the filtrate to a 2 liter flask containing 3.5 grams of a borohydride exchange resin (about 0.07 grams of resin per gram of morphine base). The slurry contained in the 2 liter flask was then stirred, heated and maintained at 50° C.

After approximately 20 hours, the resin was filtered and the solution was returned to the flask and heated to 60° C. Next, water was added to the flask over about 15 minutes during which time a precipitate formed. The slurry was stirred for about 1 hour and then cooled to 0-5° C. over a 1 hour period. The precipitate was filtered, washed with 100 ml of a cold 20% water/methanol solution, transferred to a crystallizing dish, and placed in a vacuum oven at 60° C. for approximately 2 hours before being bottled. The product was determined to be about 95.07% by weight (liquid chromatography) morphine free base (5.85% by weight water by Karl Fischer and 0.05% by weight methanol by gas chromatography) and contain 6.7 ppm ABUK.

Example 8

Morphine Free Base Using Food-Grade Borohydride Resin

This experiment was intended to be a repeat of the experiment describe in Example 7 except that a food-grade base exchange resin was used to make the borohydride resin. Specifically, Rohm and Haas FPA-42 (Cl) food-grade resin having a density of 0.687 grams/ml was used in the experiment. 100 ml of the FPA-42 resin was stirred in an ice bath in 740 ml of deionized water at a temperature of 10° C. Next, 14 grams of $NaBH_4$ was added and the bath was stirred at 5-10° C. for 45 minutes after which the resin beads were filtered and washed with cold deionized water (four 100 ml increments). The beads were placed in a vacuum oven at 50 C for approximately 3 hours.

At this point the procedure described in Example 7 was repeated. The final product was determined to be about 94.77% by weight morphine free base (liquid chromatography), 6.20% by weight water (Karl Fischer), 0.04% by weight methanol (gas chromatography) and to contain 4.2 ppm ABUK.

Example 9

Morphine Free Base Utilizing Acid Pretreatment and Exchange Resin 60.78 grams of morphine base material (MW 285.34, 6.10% water, 32 ppm ABUK) 250 ml of water, and 55 ml of 51% sulfuric acid (7.28 M) were charged in a 1 liter flask fitted with a condenser apparatus, a temperature probe and a pH probe. The mixture was mechanically stirred under an inert gas of nitrogen and a temperature of 70° C. over night. Next, the solution was transferred to a beaker in an ice bath and stirred after which 50% NaOH (64 grams, 800 mmol) and 500 ml of water were slowly added. The pH was determined to be 7.90. Then 15 ml of concentrated $NH_4OH$ was added to increase the pH to 9.70. The slurry was filtered, washed with water to provide a wet cake (143.32 grams). The cake was dried in a vacuum oven at 60° C. over night resulting in 55.81 grams of an off-white powder of morphine free base containing 121 ppm ABUK.

Next, 54.71 grams of the free base were placed in a 2 liter flask fitted with a condenser apparatus, a temperature probe, a pH probe under an inert gas of nitrogen. Methanol (15 ml/gram) was charged (820 ml) to the flask as was 10.0 grams of borohydride resin. The mixture was then brought to a temperature of 50° C. for about 24 hours after which it was filtered (hot). An additional 30 ml of methanol was used to wash the resin and aid the transfer of the filtrate. The remaining solution was heated to 60° C. to which 123 ml of water was added drop-wise over 33 minutes while maintaining the temperature at greater than 58° C. The solution was stirred for about 1 hour and then cooled to 0-5 C over a 2 hour period after which it was filtered and washed with a 100 ml of cold methanol:water mixture (80:20). The wet filtrate cake was placed in a vacuum oven at 50° C. resulting in a white crystal morphine base product containing 5 ppm ABUK.

After two months of storage under air at room temperature the product was determined to have 117 ppm ABUK, 5.70% by weight water and 0.08% by weight methanol.

Next, 10.00 grams of the morphine base containing 5 ppm ABUK and 180 ml of absolute ethanol were added to a 500 ml flask, fitted with a condenser apparatus, a temperature probe, under an inert gas of nitrogen. The mixture was heated to 65° C. at which point all of the free based was observed to be dissolved. Next, 17.5 ml of 1 M $H_2SO_4$/5 M $H_2O$ in ethanol was added to the flask over 2 minutes after which the mixture was stirred for 1 hour at 65-70° C. The temperature was then reduced and the flask was placed in an ice bath for cooling to less than 5° C. The mixture, now containing a morphine sulfate precipitate, was filtered, washed with 75 ml of ethanol and placed in a vacuum oven at 60° C. The morphine sulfate product was determined to contain 92 ppm ABUK.

Example 10

Morphine Sulfate Methanol Solvate

In a related experiment as that described in Example 9, 9.0 ml of water and 5.55 ml of concentrated sulfuric acid, were added to a 100 ml volumetric flask containing 80 ml of methanol. The flask was cooled in an ice bath to achieve room temperature and additional methanol was added to achieve a 100 ml volume in order to provide a 1 M $H_2SO_4$/5 M $H_2O$ methanolic solution.

Next, 10.00 grams of morphine base containing 5 ppm ABUK and 150 ml of methanol were mixed at 55° C. dissolving the base. Then, 17.5 ml of the above methanolic solution was added over approximately 5 minutes. No precipitate formed. A small amount of the dissolved morphine/methanolic solution was withdrawn, scratched until a seed formed, and then added to the solution. A precipitated formed and was stirred at 55° C. for 45 minutes at which time the heat was turned off and the slurry allowed to cool to 26.8° C. before placing it on an ice bath to achieve a temperature of less than 5° C. The precipitate was filtered and washed with cold methanol before placing it in a vacuum oven at 40° C. The product was determined to yield 85.5% morphine sulfate (as non-solvate, non-hydrate, 2 morphine $H_2SO_4$ basis). The molecular weight of the morphine sulfate methanol solvate was 750.85 having 8.53% by weight methanol and 2.40% by weight water, and containing 2 moles of methanol and 1 mole of water per mole of morphine sulfate.

After 2 months under air at room temperature the ABUK level was determined to be 11 ppm. The sample also contained 8.75% by weight methanol and 2.85% by weight water. The sample was analyzed by XRPD using a Bruker XRD Model D8 Advance instrument and the results are provided herein as FIG. 4 and Table A. As shown herein as FIG. 5, a DSC analysis was also performed on the sample using a TA Instruments DSC Model Q10.

Example 11

Stability Study

In yet another experiment, the morphine sulfate methanol solvate described in Example 10 was stored at room temperature for about 1 month after which the product was divided into two samples and separately placed in vials with the first sample sealed in a vial under air and the second sample sealed in a different vial under nitrogen. Both samples were then heated to 60° C. for about 1 month. The first sample (stored in air for about 2 months) was determined to contain 7.72% by weight methanol, 5.09% by weight water and 59 ppm ABUK whereas the second sample (stored in air for 1 month and nitrogen for 1 month) contained 7.21% by weight methanol, 5.18% by weight water and 21 ppm ABUK.

While the invention has been described in detail and with reference to specific examples thereof, it will be apparent to one skilled in the art that various changes and modifications can be made therein without departing from the spirit and scope thereof.

It has also been determined that ABUK level increases significantly (>100 ppm) when low ABUK morphine base is converted to a salt (e.g., morphine sulfate). However, the Examples above demonstrate that ABUK precursor impurities in a morphine starting material can be converted to ABUK (e.g., morphinone) and further that the ABUK can be significantly removed by contacting the material with an anion exchange resin. Surprisingly, it has been discovered that, when low ABUK morphine base is converted to morphine sulfate methanol solvate, the ABUK levels do not increase significantly. In other words, when the sulfate is made in methanol instead of water, the ABUK levels no longer increase significantly. In an effort to confirm this finding, morphine sulfate was made in ethanol instead of methanol. However, it was discovered that morphine sulfate made in ethanol results in increased ABUK levels. It was therefore concluded that methanol, but not ethanol, can be used to make a morphine sulfate solvate having low levels of ABUK.

What is claimed is:

1. A method of making a morphine sulfate methanolic solvate composition comprising:
    mixing a morphine free base composition with methanol to form a solution; and
    adding a liquid comprising sulfuric acid to the solution to form a morphine sulfate methanolic solvate precipitate.

2. The method according to claim 1 further comprising the step of heating the solution to at least 50° C.

3. The method according to claim 1, wherein the liquid further comprises water.

4. The method according to claim 1 further comprising the steps of:
    removing a portion of the solution after the addition of the liquid;
    inducing crystallization in the removed solution to form crystals; and
    returning the removed solution containing the crystals to the solution.

5. A method of making a morphine sulfate methanolic solvate composition comprising:
    mixing a starting composition comprising morphine and α,β-unsaturated ketones with methanol to form a solution whereby at least a portion of the starting composition is dissolved in the methanol;
    contacting a borohydride exchange resin with the solution;
    separating the resin from the solution;
    adding water to the solution to produce a resultant morphine free base composition having a level of α,β-unsaturated ketones less than the starting composition;
    mixing the resultant morphine free base composition with methanol to form a second solution; and
    adding a liquid comprising sulfuric acid to the second solution to form a morphine sulfate methanolic solvate precipitate.

6. The method of claim 5 further comprising the step of heating the starting composition and methanol during the mixing step.

7. The method according to claim 5, wherein the starting composition is a free base.

8. The method of claim 5, wherein the starting composition completely dissolves in the methanol.

9. The method of claim 6, wherein the starting composition and methanol are heated to at least 50° C.

10. The method of claim 5 further comprising adding activated carbon prior to or during the mixing step and subsequently removing the activated carbon.

11. The method according to claim 5, wherein the contacting step is carried out for a period of at least 10 hours.

12. The method of claim 5 further comprising a treatment step prior to the mixing step.

13. The method of claim 12, wherein the treatment step comprises:
    combining concentrated poppy straw and methanol to form a mixture;
    heating the mixture;
    combining water and the mixture to form a precipitate; and
    filtering the precipitate to provide the starting composition.

14. The method of claim 12, wherein the treatment step comprises:
  mixing a composition comprising morphine with water and an acid until at least a portion of the composition dissolves;
  heating the mixture for a time sufficient for the composition to react with the water and acid; and
  adding sufficient base until a precipitate forms; and
  filtering the precipitate to provide the starting composition.

15. Crystalline morphine sulfate methanolic solvate containing less than 25 ppm of $\alpha,\beta$-unsaturated ketones.

16. Crystalline morphine sulfate methanolic solvate exhibiting an x-ray powder diffraction pattern substantially as shown in FIG. 4.

17. Crystalline morphine sulfate methanolic solvate exhibiting an x-ray powder diffraction pattern having at least one peak in degrees 2θ selected from 9.3, 9.6, 10.7, 13.5, 14.3, 16.4, and 23.5.

18. The crystalline morphine sulfate methanolic solvate of claim 17, wherein the solvate exhibits an x-ray powder diffraction pattern having at least three peaks in degrees 2θ selected from 9.3, 9.6, 10.7, 13.5, 14.3, 16.4, and 23.5.

19. The crystalline morphine sulfate methanolic solvate of claim 17, wherein the solvate exhibits an x-ray powder diffraction pattern having peaks in degrees 2θ at 9.3, 9.6, 10.7, 13.5, 14.3, 16.4, and 23.5.

20. Crystalline morphine sulfate methanolic solvate exhibiting a differential scanning calorimetry curve substantially as shown in FIG. 5.

21. Crystalline morphine sulfate methanolic solvate having an onset of melt temperature of about 137° C. by differential scanning calorimetry.

22. Crystalline morphine sulfate methanolic solvate having a melting point temperature of about 143° C. by differential scanning calorimetry.

23. The crystalline morphine sulfate methanolic solvate of claim 17, wherein the solvate contains about two molecules of methanol and about one molecule of water for every molecule of morphine sulfate.

24. A method of making a morphine sulfate compound comprising:
  mixing a morphine free base composition with methanol to form a solution;
  adding a liquid comprising sulfuric acid to the solution to form a morphine sulfate methanolic solvate precipitate; and
  drying the morphine sulfate methanolic solvate in the presence of water vapor, such that methanol molecules are removed and replaced with water molecules to provide the morphine sulfate compound.

25. A composition for treating pain comprising the morphine sulfate compound made by claim 24 and at least one pharmaceutically acceptable excipient.

26. A method for treating pain comprising administering to a mammal in need thereof the composition of claim 25.

27. A morphine sulfate compound comprising a crystalline morphine product containing water and methanol molecules and containing less than 0.15% by weight methanol.

28. The morphine sulfate compound of claim 27 containing less than 0.10% by weight methanol.

29. The morphine sulfate compound of claim 27 containing less than 0.05% by weight methanol.

30. A composition for treating pain comprising the morphine sulfate compound of claim 27 and at least one pharmaceutically acceptable excipient.

31. A method for treating pain comprising administering to a patient in need thereof the composition of claim 30.

32. The method of claim 24 further comprising, between the adding and drying steps, storing the morphine sulfate methanolic solvate.

33. The method of claim 32, wherein the morphine sulfate methanolic solvate is stored for a period of time between two weeks and six months.

34. The method of claim 32 further comprising formulating the morphine sulfate compound into a pharmaceutical composition by combining the morphine sulfate compound and at least one pharmaceutically acceptable excipient.

35. The method of claim 34, wherein the formulating step is carried out within one hour after the completion of the drying step.

36. The method of claim 35 further comprising storing the pharmaceutical composition.

37. The method of claim 36, wherein the step of storing the pharmaceutical composition is done in an inert atmosphere.

* * * * *